United States Patent [19]

de Jonge et al.

[11] Patent Number: 4,607,029
[45] Date of Patent: Aug. 19, 1986

[54] NOVEL SODIUM AMOXICILLIN PREPARATIONS

[75] Inventors: Hayo de Jonge, Heemstede; Jan W. Groenendaal, Haarlem; Gerrit J. Sijbrands, Zandvoort; Annita Bagerman-Deetman, Oosterhout, all of Netherlands

[73] Assignee: Gist-Brocades N.V., Delft, Netherlands

[21] Appl. No.: 726,027

[22] Filed: Apr. 23, 1985

Related U.S. Application Data

[63] Continuation of Ser. No. 481,338, Apr. 1, 1983, abandoned, which is a continuation of Ser. No. 80,051, Sep. 28, 1979, abandoned.

[30] Foreign Application Priority Data

Oct. 3, 1978 [NL] Netherlands .......................... 7809986
Jan. 3, 1979 [NL] Netherlands .......................... 7900021

[51] Int. Cl.$^4$ ............................................. A61K 31/43
[52] U.S. Cl. ..................................................... 514/197
[58] Field of Search .......................................... 514/197

[56] References Cited

U.S. PATENT DOCUMENTS 4,024,244 5/1977 Love ................................... 424/271
4,029,804 6/1977 Clark et al. ......................... 424/271

*Primary Examiner*—Jerome D. Goldberg
*Attorney, Agent, or Firm*—Bierman, Peroff & Muserlian

[57] ABSTRACT

Novel sodium amoxicillin preparations which are easily converted into stable, suitably injectable solutions which are free of allergic reactions-causing chemicals and which contain besides sodium amoxicillin, a small amount of sodium hydroxide and optionally also a small amount of sodium chloride, and a process for their preparation and a process for the preparation of aqueous sodium amoxicillin containing injection solutions. The sodium amoxicillin preparations are prepared by the as fast but gradual addition as possible of an excess of sodium hydroxide to a suspension of amoxicillin trihydrate in water until the amoxicillin has completely dissolved, whereafter optionally a part of the excess of base is immediately neutralized with hydrochloric acid while the temperature is kept between 0°–30° C., followed by sterile filtration of the obtained solution, freezing the solution and freeze drying the obtained solid in flasks or in bulk.

5 Claims, No Drawings

NOVEL SODIUM AMOXICILLIN PREPARATIONS

PRIOR APPLICATION

This application is a continuation of copending U.S. patent application Ser. No. 481,338 filed Apr. 1, 1983 which in turn is a continuation of U.S. patent application Ser. No. 080,051 filed Sept. 28, 1979, both now abandoned.

STATE OF THE ART

A freeze drying process is known from e.g. the Dutch Published Patent Application No. 7,707,494 which discloses a process consisting of freeze drying a solution of sodium amoxicillin in a solvent system containing water and as a stabilizer, at least 5% by weight, of a secondary or tertiary alkanol with 4 or 5 carbon atoms which is soluble in water at 25° C. while preferably 4–50% by weight of the secondary or tertiary alkanol is present. The tertiary alkanol is preferably t-butanol, however there is indicated that the solvent system may also contain small amounts of other pharmaceutically acceptable solvents such as primary alcohols. A disadvantage of these preparations is the presence of bodily strange solvent residues which, although they are toxicologically acceptable, may give rise to several undesired side reactions after administration of the final injection preparation. The content of these solvent residues may amount up to 6% of the dry product.

It was also known to prepare crystalline cephalosporins suitable for parenteral administration which are prepared by freeze drying, e.g. U.S. Pat. No. 4,029,655 and more especially Belgian Pat. No. 861,135, relating to the preparation of stable sodium cephalotin powder for parenteral administration by freeze drying of a previously prepared solution of sodium cephalotin in a 2–10% alcohol or acetone containing aqueous solution. Also to be mentioned is Dutch Published Patent Application No. 7,712,823, relating to the preparation of crystalline, easily dissolving sodium cephazolin with freeze drying of 2–25% of alkanol containing aqueous solution, while cooling the starting solution slowly. However, the same disadvantages as mentioned hereinbefore hold for the so obtained preparations.

On the other hand, much activity has been directed to the search for suitable amoxicillin preparations which may be easily converted to the usual, sufficiently stable injection solutions and which moreover have to be sufficient stable in the dry form as can be seen from the large number of patent publications which have appeared in the last few years. It will be appreciated from this patent literature that the general developed conception of people skilled in the art is, that for the preparation of injectable preparations of amoxicillin, the usual methods as applied to formerly developed semi-synthetic penicillins such as ampicillin, certainly cannot be used without any additional measures with reference to the clearly different chemical and physical properties of amoxicillin.

Therefore, all sorts of proposals have been made to come to an adapted preparation of compositions which contain the usual alkali metal salts of amoxicillin and derivatives thereof and the people skilled in the art seem inclined to search for well conversable and well injectable preparations containing amoxicillin salts having alternative cations.

For example, Dutch Published Patent Application No. 7,509,701 discloses a process for the preparation of the choline salt and the N-methyl-D-glucamine salt of amoxicillin, respectively, according to methods known per se on their own, while in Dutch Published Patent Application No. 7,509,698 the preparation of the arginine salt of amoxicillin is disclosed. These salts of amoxicillin should lead to novel, non-toxic, parenterally administrable forms of amoxicillin while keeping the antibiotic properties. Moreover, on page 1 of the application, it is explicitly mentioned that amoxicillin itself as well as its salts which are known up to now cannot be administered parenterally in a satisfactory way. Also, in Example 4 of Japanese Published Patent Application No. 51,032,723, the preparation is disclosed of a suitable injectable solution containing amoxicillin and the sodium salt of glycine.

In German Published Patent Application No. 2,540,523 a process is described for the preparation of salts of D-α-carboxyamino-p-hydroxybenzylpenicillin with the purpose of the preparation of satisfactory injectable amoxicillin preparations. But, also page 2 of this application, there is again explicitly stated that the preparation of injectable amoxicillin preparations appeared to be much more difficult than was initially expected by skilled people which was attributed to the instability of amoxicillin containing solutions caused by the decomposition of amoxicillin salts in aqueous solutions. According to this last mentioned patent application, preferably mixtures of the sodium salt of amoxicillin and the disodium salt of D-α-carboxyamino-p-hydroxybenzyl penicillin would have to be used.

In Dutch Published Patent Application No. 7,602,180, a process for the preparation of an injectable preparation of amoxicillin is described which possesses a good stability and is well tolerated at administration of a ready injectable solution. This preparation is composed of a powder which may be easily converted into an injectable preparation by addition of an aqueous vehicle. The powder consists of fine particles of amoxicillin trihydrate coated with a dispersing agent, the ratio between amoxicillin trihydrate and dispersing agent being of from 1000:1 to 20:1. The fine particles under consideration should have a diameter of from $2\mu$ to $20\mu$ on average, while at least 95% should have a diameter between $0.5\mu$ and $50\mu$, while from 10 up to 100% of the surface should have been coated with dispersing agent. Proposed dispersing agents are a mixture of compounds containing at least one polymeric material soluble in water with an average molecular weight of from 6000 to 40,000 such as polyvinylpyrrolidone, vinylpyrrolidone, vinylacetate copolymers, sodium carboxymethylcellulose, polyvinylalcohol, dextran and sodium alginate and preferably polyvinylpyrrolidone, and a wetting agent such as lecithin, phospholipide, sorbitan fatty acid esters and more particularly lecithin.

For the same reasons there was research in the direction of chemically modified amoxicillin derivatives which decompose in the body so that amoxicillin again is formed. In this connection, there may be referred to U.S. Pat. No. 4,035,381 and Dutch Published Patent Application No. 7,701,480.

OBJECTS OF THE INVENTION

It is an object of the invention to provide sodium amoxicillin compositions having an excellent degree of stability, as well in the form of a dry preparation as in solution.

It is another object of the invention to provide a novel process for the preparation of stable sodium amoxicillin compositions.

These and other objects and advantages of the invention will become obvious from the following detailed description.

THE INVENTION

The novel compositions of the invention which may be easily converted into stable, injectable solutions free of allergic reaction-causing chemicals comprises sodium amoxicillin and an effective amount of sodium hydroxide.

The improved, stable sodium amoxicillin compositions of the invention may be prepared by gradually adding but as rapidly as possible an excess of sodium hydroxide to an aqueous suspension of amoxicillin trihydrate until the amoxicillin is completely dissolved, optionally immediately neutralizing a portion of the excess sodium hydroxide with a hydrochloric acid solution at temperatures between 0° and 30° C., preferably at 20°-25° C., subjecting the solution to sterile filtration, freezing the solution and freeze drying the resulting solid in either bulk or in injection flasks. Preferably, a greater excess of sodium hydroxide is used and then partly neutralized with a hydrochloric acid solution.

Preferably, the starting amounts of amoxicillin trihydrate, of sodium hydroxide and of hydrochloric acid are selected so that a final concentration of 2.5-15% by weight of sodium amoxicillin and more preferably of <5% by weight is obtained. The clear solution of the amoxicillin salt may be obtained by gradual addition, to avoid local undesired base concentrations asmuch as possible, of an aqueous solution of sodium hydroxide with vigorous stirring to a suspension of amoxicillin trihydrate in water until a molar excess of sodium hydroxide is reached of at most 15 mol % and preferably greater than 9%, whereafter the excess sodium hydroxide is neutralized as fast as possible until at least about 3 mol % and preferably about 5 mol % of sodium hydroxide is present in excess. As a result of this partial neutralization, about 10 mol % of sodium chloride is then present in the solution, too.

According to an alternative embodiment, a clear solution may be obtained by the addition of a solution of sodium hydroxide with vigorous stirring to a suspension of amoxicillin trihydrate in water until a molar excess of about 5 mol % of sodium hydroxide is reached. However, for the preparation of relatively larger batches and higher concentrations of sodium amoxicillin, a larger initial excess of sodium hydroxide is used which is immediately partly neutralized by the addition of hydrochloric acid solution.

It will be appreciated that the amoxicillin solution has to be filtered, frozen and freeze dried in flasks or in bulk under aseptical conditions. If the solution is frozen and freeze dried in flasks, preferably injection flasks and rubber stoppers especially designed for freeze drying are used. The flasks are filled so that they contain an amount of 0.10-5 g and preferably 0.25, 0.5 and 1 g of the dry final sodium amoxicillin preparation.

The freezing and freeze drying may be carried out by the use of equipment which is generally suitable for these purposes such as a Sec. Froid SA CH-1024 lyolab D laboratory freeze drying equipment or a Leybold production freeze drying equipment. It will be appreciated that the freezing may also take place outside the actual freeze drying equipment.

For the freezing step, the obtained amoxicillin solution is preferably cooled over 0.5 to 2.5 hours to from $-20°$ C. to $-70°$ C. and more preferably cooled in 0.5 to 1.0 hour to from $-20°$ to $-30°$ C. at atmospheric pressure. Subsequently, the pressure is reduced to 9.0-12.0 N/m$^2$ and preferably to 10 N/m$^2$ and the temperature is slowly raised to 0° C. over 24-30 hours, preferably over about 25 hours, while the vacuum slowly raises to about 8N/m$^2$. Then the temperature is raised by heating to ambient temperature over 4-5 hours while maintaining the vacuum raising to 8N/m$^2$.

According to an alternative and more preferred embodiment of the process, the freezing and freeze drying of the solution of amoxicillin after sterile filtration also may take place in bulk by pouring this solution under aseptical conditions into e.g. stainless steel trays or plates of sterilized plastic foil supported by a sterilized metal frame and both having an upstanding rim of a height up to about 4 cm. The plastic foil has to be fitted so that an optimal contact of the solution with the drying plates is obtained. The final level of the liquid may be 0.5 to 3 cm and is preferably about 1 cm. The drying plates of the freeze drying equipment are preferably previously cooled to a temperature of from $-25°$ C. to $-50°$ C. and preferably to about $-40°$ C.

The cooling capacity of the freeze drying equipment has to be sufficiently large enough to freeze the solution having a level of 0.5 to 3 cm, preferably of 1 to 2 cm, within 60-30 minutes, preferably within 50-40 minutes to a temperature of from $-10°$ C. to $-30°$ C., preferably of from $-15°$ C. to $-20°$ C. The time between the suspension of the amoxicillin trihydrate and the closing of the freeze drying equipment after bringing the flasks or pouring out the solution onto the plates preferably does not amount to more than 30 minutes while the time which is necessary for the preparation of the solution, filtration, filling of flasks and/or bringing the solution into the freeze drying equipment and freezing preferably does not amount to more than 90 minutes.

It will be appreciated that the freezing may also take place outside the actual freeze drying equipment. According to a specific example of the embodiments of the alternative of freeze drying in bulk as described hereinbefore, the condensor is turned on and the pressure is lowered in the drying room to about 100 N/m$^2$ as soon as the formation of ice occurs and the temperature of the product has been lowered to about $-10°$ C. After 0.5-2 hours at the same pressure, the cooling of the plates is turned off and the heater of the drying plates is turned on whereby the temperature of the heating liquid is raised slowly and linearly within 60 minutes to room temperature. The subsequent drying period amounts to 20-40 hours, preferably about 30 hours. During the whole freezing and freeze drying process, the temperature of the product, of the heating liquid of the plates, of the drying plates themselves and of the condensor and the pressure in the drying room and in the condensor are recorded. There after, drying may take place during 5-8 hours at a temperature of 30° C. of the drying plates.

The vacuum of the drying room is eliminated by the addition of dry nitrogen which has been filtered through a 0.2 μm filter, whereafter the dried sodium amoxicillin is removed from the drying room and is stored under nitrogen at a temperature of 0°-10° C. under aseptical conditions. Then, the obtained sodium amoxicillin is ground under aseptical conditions to a particle size, at which is sieve of 2 mm may be passed, whereafter amounts of 250, 500 or 1000 mg are filled into sterilized injection flasks under dry and aseptical conditions and then the flasks are closed and sealed in the usual way.

Surprisingly, it was now found that sodium amoxicillin preparations which contain 4.5–3.0% and preferably about 3.5% by weight of decomposition products and which show an improved stability, as well in the form of a dry preparation as in solution may be prepared by the process as described hereinbefore, while stabilizers or organic solvents which may cause the undesired side phenomena are avoided.

According to the alternative embodiment of the present process with previously filled flasks, flasks containing 0.5 g of the final dry preparation are preferably prepared by filling the flasks with 10 ml of a 5% by weight of a sodium amoxicillin solution, freezing and freeze drying, or flasks containing 1.0 g of the final preparation are prepared by filling the flasks with 20 ml of a 5% by weight solution of sodium amoxicillin, freezing and freeze drying.

For 500 mg of sodium amoxicillin preparation, 5–12 mg and preferably 7–8 mg of sodium chloride are present in the final preparation.

It is true, that German Patent Application No. 2,623,835 shows that it was known to prepare sodium ampicillin by means of freeze drying by addition of an aqueous solution of an equimoleculair amount or an amount up to 10% deficit of sodium hydroxide, sodium bicarbonate or sodium carbonate to an aqueous suspension of ampicillin, at a temperature not higher than 4° C. so that not any too high concentration of the base is occcuring locally, immediate sterile filtration of the obtained solution and the freezing and lyofilization of the filtrate. However, due to the well known differences in chemical and physical properties between ampicillin and amoxicillin, it was certainly not predictable to one skilled in the art that an applicable preparation method for the preparation of sodium ampicillin could be used in any analogous manner for the preparation of practically pure sodium amoxicillin. Where so many efforts had already failed or had led to only partial results, there is no longer talk of a predictability of the suitability of a novel method.

Neither the conceptions of the people skilled in this art of penicillin chemistry, which have been indicated earlier as being valid at that time as was stated in or appeared implicitly from the recently proposed solutions of the problem to reach suitable injection preparations of amoxicillin, nor the indications given in German Pat. No. 2,623,835, stating that at most an equimolecular amount of sodium hydroxide could be applied and the use of an excess of base had to be prevented, may lead to a man skilled in the art to the idea to apply greater amounts of sodium hydroxide than those which seem strictly necessary. Moreover, this measure of the invention could certainly not be regarded as obvious because of the contents of Canadian Journal of Pharmaceutical Sciences, Vol. 12 (1977) No. 3, p. 83, right column, from which it appears that the pH of the maximal stability of amoxicillin is 5.77 and that the rate of decomposition does not seem to increase until the pH is brought below 5.5 or above 6.5, while the optimal conditions for the stability of aqueous solutions of amoxicillin lye in the range from pH 5.8 to 6.5 with a citrate buffer, and while a pH of 8–9 is temporarily reached according to the presently proposed process. The preparations obtained according to the present invention may be converted to the desired aqueous injection solutions according to methods known per se.

In the following examples, there are described several preferred embodiments to illustrate the invention. However, it is to be understood that the invention is not intended to be limited to the specific embodiments.

EXAMPLE 1

64.5 mmoles (27.06 g) of amoxicillin trihydrate were suspended with an Ila homogenizer of the type X-1020 at a temperature of 20°–25° C. within 5 minutes and in about 350 ml of sterile pyrogen free water and then 74.2 mmoles (2.97 g) of sodium hydroxide in 50 ml of sterile pyrogen free water were added dropwise with vigorous stirring over 5 minutes. The resulting clear solution was immediately neutralized with 6.45 mmoles (12.9 ml of 0.50 N) of hydrochloric acid and the solution was transmitted into a 500 ml measuring flask and sterile pyrogen free water was added for adjustment of the exact volume. The solution was filtered bacteria-free under aseptical conditions with, for example, a stainless steel Sartorius filter equipment of the type of 16245 provided with a Sartorius membrane filter having a pore size of 0.2 $\mu$m of the type 11307 connected to a Sartorius air compressor of the type AL-17. 10 ml portions of the filtered solution were filled into 20 ml injection flasks with a Brand dispensor of the type 7050-15 under aseptical conditions. Temperature sensors of the Sec. Froid freeze drying equipment type lyolab D were fixed in three flasks and the flasks were provided with rubber stoppers which were especially made for freeze drying. The filled flasks were transmitted on one of the three drying plates of the drying room after the plates have been adjusted to a temperature of $-20°$ to $-25°$ C. by means of the freezing bath and then the drying room was flushed with about 600 l/hour of nitrogen gas filtered through 0.2 $\mu$m. A temperature sensor was connected to the drying plate on which the flasks were placed. During the whole process thereafter, the temperature of the three flasks and of the drying plate was recorded with a Sec. Froid recorder.

In FIG. 1, the course of respectively the temperature of the product, the temperature of the drying plate and the absolute pressure with the time, are indicated from the start of the freezing as a characteristic example of the present process. The course of the temperature of the product is indicated by means of curve (a), the course of the temperature of the drying plate by means of curve (b) and the course of the absolute pressure by means of curve (c).

Point (1) in curve (c) indicates the turning on of the vacuum pump, while point (2) in curve (b) indicates the turning on of the heating of the drying plate. After the formation of ice in the flasks had occured and the temperature had decreased within 1 hour to $-20°$ C., the drying room was evacuated after the nitrogen supply has been cut off and the condensor was turned on.

The cooling of the drying plates was turned off after which the plates slowly rose in temperature and the drying period took about 24 hours. The thermostat for the plate heating was turned on after the product-temperature had been raised above 10° C. and had become equal to the plate temperature and after ice in the flasks could not be seen. The temperature of the thermostat was adjusted to 30° C. and drying was carried out during about 5 hours. The thermostat, vacuum pump and the cooling of the condensor were turned off and the vacuum of the drying room was terminated by supplying nitrogen filtered through a 0.2 μm filter. The flasks were closed in the freeze drying equipment and after removal from the freeze drying equipment, the flasks were sealed with aluminium folding capsules with a Fermpress handcrimper type H-207.

The resulting charges were then analyzed for the content of sodium amoxicillin, the content of decomposition products, the water content, the content of sodium chloride, clearness of the solution, pH of the solution, infra red spectrum and PMR spectrum.

Analyzing results of the prepared batch were the following:
content (microbiological) of sodium amoxicillin: 93.3%
content (mercurimetrical) of sodium amoxicillin: 94.4%
content of decomposition products (mercurimetrical): 3.6%
solubility: 10 g/v % solution in water remained clear for at least 1 hour
pH of freshly prepared solution in water 10 g/v %: 8.7%
water content (Karl Fischer): 2.2%

The structure of sodium amoxicillin was confirmed by IR and PMR spectra.

EXAMPLE 2

Using the procedure of Example 1, several charges of sodium amoxicillin compositions were prepared whereby a number of parameters were varied as compared with the corresponding ones in Example 1. The results obtain according to Examples 1 and 2 are summarized in Table 1 and in FIGS. 2, 3 and 4.

of decomposition products measured by mercurimetric titration and time were plotted.

The freeze dried starting preparation used for FIG. 3 was prepared by suspending amoxicillin trihydrate in water at room temperature, followed by addition of a 15 mol % excess of sodium hydroxide, neutralization with a hydrochloric acid solution to a 5% mol excess of sodium hydroxide, filtration of the obtained solution with a 0.2μ filter and filling into F 20 flasks of 10 ml a 5% by weight solution of sodium amoxicillin followed by freezing and freeze drying. The flasks containing the freeze dried preparation were stored at 5° C. for 10 weeks.

EXAMPLE 3

2.58 mol (1082 g) of amoxicillin trihydrate were suspended at 20°–25° C. over 10 minutes with a Vibro Mischer in about 12.5 l of pyrogen free water and 2.97 mol (119 g) of sodium hydroxide in 2 l of pyrogen free water were added at a rate of about 380 ml/min with vigorous stirring. The clear solution was immediately thereafter neutralized with 0.26 mol (516 ml 0.50 N) of hydrochloric acid and the solution was adjusted with pyrogen free water to 20.0 l (20.28 kg) and mixed. The solution was filtered under aseptical conditions with a Seitz filter having 9 EKS plates of 20×20 cm and the filtrate was collected under aseptical conditions in 4 l flasks. The solution was transmitted under aseptical conditions onto sterilized plastic foil which was placed on the drying plates and temperature sensors were fixed and the drying room was closed. The foil had previ-

| | | | | | sodium amoxicillin (mercuro-metrically determined) % | sodium amoxicillin theorethical % | decomp. products (mercuri-metrically determined) % | | | |
|---|---|---|---|---|---|---|---|---|---|---|
| charge | amount | temp. of preparation of solution °C. | excess of NaOH before neutralization mol % | excess NaOH after neutralization mol % | | | | water content % | 10 g/v % solution clearness | measured pH |
| A | 20 flasks 0.5 g | 20–25 | 15 | 5 | 94.3 | 95.8 | 3.6 | 2.2 | clear | 8.7 |
| B | 20 flasks 0.5 g | 0–5 | 20 | 10 | 95.2 | 95.3 | 3.2 | 2.3 | clear | 8.9 |
| C | 10 flasks 1 g | 0–5 | 30 | 15 | 92.1 | 94.8 | 5.2 | 1.6 | clear | 9.0 |
| D | 10 flasks 1 g | 20–25 | 15 | 5 | — | — | — | — | troubled | 8.75 |
| E | 50 flasks 0.5 g | 0–5 | 20 | 10 | 94.1 | 95.1 | 5.0 | 2.5 | clear | 8.9 |
| F | 20 flasks 1 g | 0–5 | 30 | 15 | 91.7 | 93.8 | 5.3 | 2.6 | clear | 9.05 |
| G | 50 flasks 0.5 g | 20–25 | 15 | 5 | 95.8 | 95.8 | 3.3 | 2.3 | clear | 8.7 |
| H | 20 flasks 1 g | 20–25 | 15 | 7 | 93.9 | 96.3 | 4.8 | 1.8 | clear | 8.8 |

The characterizing amoxicillin structure of all tested charges could be confirmed by IR and PMR spectra.

In FIG. 2, the relation between the stability of a 5% and 10% by weight solution of sodium amoxicillin before freezing and freeze drying and the time has been expressed, whereby the curve (d) corresponds to a 10% by weight solution of sodium amoxicillin and curve (e) corresponds to a 5% by weight solution. Along the axis, the percentage of decomposition products measured by mercurimetric titration and time were plotted.

In FIG. 3, the relation between the stability of freeze dried sodium amoxicillin dissolved in water and time have been expressed whereby the curve (f) corresponds to a 20% by weight solution, curve (g) corresponds to a 10% by weight solution and curve (h) corresponds to a 5% by weight solution. Along the axis, the percentage ously been fixed on the drying plates and had an upstanding rim of a height of 4 cm supported by a sterilized metal frame work, while the foil had been secured so that an optimal contact was obtained between the solution with the drying plates. The drying plates of the freeze drying equipment were preferably previously cooled to a temperature of −40° C. and the cooling capacity of the freeze dryer had to be selected large enough to freeze a solution having a level of about 1 cm within 60 minutes to −10° C.

The time between the suspension of the amoxicillin trihydrate and the closing of the freeze drying equipment after pouring out the solution onto the plates did not exceed 30 minutes. As soon as a formation of ice had occured and the temperature of the product was lowered to about −10° C., the condensor was turned on and the pressure in the drying room was lowered to 1 Torr. After the pressure in the drying room has been held for 1 hour at 1 Torr, the cooling of the plates was turned off. Heating of the drying plates was turned on whereby the temperature of the heating equipment was slowly and linairly raised to 25° C. over 60 minutes. During the drying period which took about 35 hours, the temperature of the product, the heater of the plates, the drying plates themselves, and the condensor and the pressure in the drying room and in the condensor were recorded. By measuring the pressure differences between the drying room and condensor made during short turning off of the connection between drying room and condensor, there was determined when the product was practically dry. The after drying process with a diffusion pump was begun and took 6 hours. At the same time, the heating of the drying plates was adjusted to 30° C. and the vacuum of the drying room was terminated by supplying dry nitrogen filtered through a sterilized 0.2 μm filter. The dried sodium amoxicilinn was removed from the drying room and stored under nitrogen at 5° C. under aseptical conditions.

With the foregoing process, three additional charges of sodium amoxicillin were freeze dried and the four charges of 1 kg were ground with a milling equipment such as a Peppink mill under aspetical conditions until a sieve of 2 mm could be passed. The charges were combined and quantities of 250, 500 or 1000 mg were placed in sterilized injection flasks with e.g. a Hofflicher Karg filling equipment under dry and aseptical conditions. Under the same conditions, the flasks were provided with sterilized rubber stoppers and sealed with aluminum folding capsules. The analysis results of the prepared combined charge were as follows:

content (microbiological) of sodium amoxicillin: 931 μg/mg
content (mercurimetrical) of sodium amoxicillin: 94.1%
content (mercurimetrical) of decomposition products: 3.7%
solubility: 10 g/v % solution in water remained clear for at least 1 hour.
pH of a freshly prepared solution in water 10 g/v %: 8.8
water content (Karl Fischer): 2.9%

EXAMPLE 4

2.58 mol (1083 g) of amoxicillin trihydrate containing less than 1% by weight of decomposition products were suspended at 20°–25° C. over 10 minutes with vigorous mixing with a Vibro Mischer in about 14 liters of pyrogenfree water and a sodium hydroxide solution containing 2.72 mol (108.73 g) in 2 liters of pyrogren free water was then added at a rate of 350 to 400 ml/minute so that the excess of base will finally be 5.3 mol %. The clear solution was adjusted to a total weight of 20.3 kg with pyrogen free water while stirring and the pH was measured. The solution was filtered under aseptical conditions with a Seitz filter having 9 EKS plates of 20×20 cm and the filtrate was collected under aseptical conditions and transmitted into 12 previously cooled and sterilized stainless steel trays whereby each tray contained 1666 ml of the solution.

The level of the liquid in the tray was about 1 cm and the trays were placed in the drying room (two trays on one drying plate) of freeze drying equipment. The temperature sensors were fixed and the drying room was closed. The drying plates of the freeze drying equipment were preferably previously cooled for three hours to a temperature of −40° C. to −45° C.. The cooling capacity of the freeze dryer had to be large enough to freeze the solution having a level of about 1 cm within 60 minutes to −10° C. The time between the suspension of the amoxicillin trihydrate and the closing of the freeze drying equipment after pouring out the solution did not exceed 30 minutes. As soon as a formation of ice had occured under freezing at atmospheric pressure to an indicated temperature of the sensors of −40° C. to −45° C., the condensor was turned on and the pressure in the drying room was lowered to 0.3 Torr, while the cooling of the plates was continued. The plates were additionally cooled for one hour, after which the temperature of the heating liquid was raised to +45° C. over two hours. The drying process was continued until the product was practically dry.

The after drying process with a diffusion pump was started and took about 6 hours. The vacuum of the drying room was eliminated by supplying dry nitrogen filtered through a sterilized 0.2 μm filter. The dried sodium amoxicillin was removed from the drying room and stored under nitrogen at 5° C. under aseptical conditions in double walled plastic bags and samples from each plate were taken for analytical control of the desired sterility.

During the drying period which took about 30 hours, the temperature of the product, of the heater of the plates, of the drying plates themselves and of the condensor as well as the pressure in the drying room and in the condensor were recorded. By measuring the pressure differences between the drying room and the condensor made during short turning off of the connection between the drying room and condensor, it was determined when the product was practically dry.

According to the foregoing process, batches of 1 kg were prepared and these batches were ground with a Peppink mill under aseptical conditions until a sieve of 2 mm could be passed. Quantities of 250, 500 or 1000 mg were placed in sterilized injections flasks with a Hofflicher and Karg filling equipment under dry and aseptical conditions. Under the same conditions, the flasks were provided with sterilized rubber stoppers and sealed with aluminum folding capsules. The analysis results of such a prepared batch were as follows:

content (mercurimetrical) of decomposition products: 4.1%
solubility: 10 g/v % solution in water remained clear for at least one hour, while the freshly prepared solution was clear as water
color of freshly prepared solution 10 g/v %: ≦Y 6
pH of freshly prepared solution in water 10 g/v %: 8.79
color of freshly prepared solution 20 g/v %: ≦Y 5
pH of freshly prepared solution in water 20 g/v %: 8.85
water content (Karl Fischer): 3.9%
Y values were determined according to the European pharmacopee.

EXAMPLE 5

Using the procedure of Example 4, a batch of 1 kg of sodium amoxicilin was prepared and the analysis results thereof were as follows:
content (mercurimetrical) of decomposition products: 3.5%
solubility: 10 g/v % solution in water remained clear for at least one hour, while the freshly prepared solution was clear as water color of freshly prepared solution in water 10 g/v %:
≦Y 6 pH of freshly prepared solution in water 10 g/v %: 8.69 color of freshly prepared solution in water 20 g/v %:
≦Y 5 pH of freshly prepared solution in water 20 g/v %: 8.80 water content (Karl Fischer): 4.1%

EXAMPLE 6

A batch of 1 kg of freeze dried sodium amoxicillin was prepared using the process of Example 4, which essentially differed in that after the addition of the sodium hydroxide solution containing 118.7 g in 2 liters of pyrogen free water at a rate of 350 to 400 ml/minute, a part of the sodium hydroxide was immediately neutralized by addition of 500 ml of a 0.50 N hydrochloric acid solution in about one minute with vigorous stirring, giving rise to a final excess of sodium hydroxide of 5.3 mol %, and whereafter the clear solution was adjusted to a total weight of 20.3 kg with pyrogen free water and the pH was measured. The analysis results of the obtained batch were as follows:

content (mercurimetrical) of decomposition products: 4.3% solubility: 10 g/v % solution in water remained clear for at least one hour, while the freshly prepared solution was clear as water color of freshly prepared solution in water 10 g/v %:
≦Y 5 pH of freshly prepared solution in water 10 g/v %: 8.75 color of freshly prepared solution in water 20 g/v %:
≦Y 5 pH of freshly prepared solution in water 20 g/v %: 8.78 water content (Karl Fischer): 3.85%

EXAMPLE 7

Using the procedures of Example 6, a batch of 1 kg of sodium amoxicillin was prepared, and the analysis results thereof were as follows:

content (mercurimetrical) of decomposition products: 3.5% solubility: 10 g/v % solution in water remained clear for at least one hour, while the freshly prepared solution was clear as water color of freshly prepared solution in water 10 g/v %:
≦Y 6 pH of freshly prepared solution in water 10 g/v %: 8.80 color of freshly prepared solution in water 20 g/v %:
≦Y 6 pH of freshly prepared solution in water 20 g/v %: 8.88 water content (Karl Fischer): 3.3%

Various modifications of the process and products of the invention may be made without departing from the spirit or scope thereof and it is to be understood that the invention is to be limited only as defined in the appended claims.

What we claim is:

1. A process for the preparation of a dry composition consisting essentially of sodium amoxicillin and an amount of sodium hydroxide from 3 to 5% mole %, calculated on the sodium amoxicillin comprising gradually adding but as rapidly as possible an excess of 9 to 15 mole %, calculated on amoxicillin trihydrate, of sodium hydroxide to an aqueous suspension of amoxicillin trihydrate until the amoxicillin is completely dissolved, immediately neutralizing a portion of the excess sodium hydroxide with a hydrochloric acid solution at temperatures between 0° and 30° C. until the excess of sodium hydroxide is from 3 to 5 mole %, subjecting the solution to sterile filtration, freezing the solution and freeze drying the resulting solid in either bulk or in injection flasks.

2. The process of claim 1 wherein the final excess of sodium hydroxide in the final solution is about 5 mol %.

3. The process of claim 1 wherein the starting amounts of amoxicillin trihydrate, sodium hydroxide and hydrochloric acid are selected so that a final concentration of ≦5% by weight of sodium amoxicillin is reached.

4. The process of claim 1 wherein the time necessary for the preparation of the solution, filtration, optionally filling in flasks and/or the introduction of the solution in the freeze drying equipment and freezing does not exceed 90 minutes.

5. A dry sodium amoxicillin preparation obtained by the process of claim 1.

* * * * *